US012064350B2

United States Patent
Bachus et al.

(10) Patent No.: US 12,064,350 B2
(45) Date of Patent: *Aug. 20, 2024

(54) PERCUTANEOUS OSSEOINTEGRATED IMPLANT ASSEMBLY FOR USE IN SUPPORTING AN EXO-PROSTHESIS

(71) Applicants: University of Utah Research Foundation, Salt Lake City, UT (US); Joseph A. Longo, Paradise Valley, AZ (US)

(72) Inventors: Kent N. Bachus, Salt Lake City, UT (US); Sujee Jeyapalina, Salt Lake City, UT (US); James Peter Beck, Salt Lake City, UT (US); Roy Bloebaum, Salt Lake City, UT (US); Jayant P. Agarwal, Salt Lake City, UT (US); Joseph A. Longo, Paradise Valley, AZ (US); Erik Kubiak, Salt Lake City, UT (US); Brian Mueller Holt, Topanga, CA (US)

(73) Assignees: Joseph A. Longo, Paradise Valley, AZ (US); University of Utah Research Foundation, Salt Lake City, UT (US)

(*) Notice: Subject to any disclaimer, the term of this patent is extended or adjusted under 35 U.S.C. 154(b) by 116 days.

This patent is subject to a terminal disclaimer.

(21) Appl. No.: 17/717,545

(22) Filed: Apr. 11, 2022

(65) Prior Publication Data

US 2022/0296374 A1    Sep. 22, 2022

Related U.S. Application Data

(60) Continuation of application No. 16/383,363, filed on Apr. 12, 2019, now Pat. No. 11,298,231, which is a
(Continued)

(51) Int. Cl.
A61F 2/28    (2006.01)
A61F 2/78    (2006.01)
(Continued)

(52) U.S. Cl.
CPC .............. *A61F 2/2814* (2013.01); *A61F 2/78* (2013.01); *A61F 2002/0091* (2015.04);
(Continued)

(58) Field of Classification Search
CPC .......... A61F 2/2814; A61F 2002/30028; A61F 2002/30932; A61F 2002/7887
(Continued)

(56) References Cited

U.S. PATENT DOCUMENTS 4,158,895 A    6/1979    Reswick et al.
4,938,769 A    7/1990    Shaw
(Continued)

FOREIGN PATENT DOCUMENTS

CN    1437457 A    8/2003
DE    19931882 C1    5/2001
(Continued)

OTHER PUBLICATIONS

Chinese Office Action dated Jul. 28, 2017 for Chinese Application No. 2015-10080255.8.
(Continued)

*Primary Examiner* — David H Willse
(74) *Attorney, Agent, or Firm* — Veros Legal Solutions, LLP

(57) ABSTRACT

An implant assembly for a long bone is adapted to support an exo-prosthesis. The assembly includes a stem, a subdermal component and a percutaneous post. The stem has a proximal end that is adapted to be received in a surgically prepared medullary canal of the long bone, and a distal end having a surface that is adapted to promote bone ingrowth.
(Continued)

The subdermal component includes a proximal portion that is adapted for attachment to the distal end of the stem, and a fixation surface that is adapted to promote soft tissue fixation. The percutaneous post has a proximal end that is adapted to be attached to the subdermal component.

20 Claims, 6 Drawing Sheets

Related U.S. Application Data division of application No. 15/256,731, filed on Sep. 5, 2016, now abandoned, which is a continuation of application No. 14/181,029, filed on Feb. 14, 2014, now Pat. No. 9,433,505, which is a continuation-in-part of application No. 14/123,719, filed as application No. PCT/US2012/041112 on Jun. 6, 2012, now Pat. No. 9,668,889.

(51) Int. Cl.
*A61F 2/00* (2006.01)
*A61F 2/30* (2006.01)

(52) U.S. Cl.
CPC .............. *A61F 2002/30028* (2013.01); *A61F 2002/30299* (2013.01); *A61F 2002/30576* (2013.01); *A61F 2002/30589* (2013.01); *A61F 2002/30594* (2013.01); *A61F 2002/30604* (2013.01); *A61F 2002/30729* (2013.01); *A61F 2002/30784* (2013.01); *A61F 2002/30879* (2013.01); *A61F 2002/30932* (2013.01); *A61F 2002/7887* (2013.01)

(58) Field of Classification Search
USPC .......................................................... 623/32
See application file for complete search history.

(56) References Cited

U.S. PATENT DOCUMENTS

| | | |
|---|---|---|
| 5,631,011 A | 5/1997 | Wadstrom |
| 5,906,644 A | 5/1999 | Powell |
| 6,869,450 B2 | 3/2005 | Grundei |
| 7,909,883 B2 | 3/2011 | Sidebotham |
| 11,298,231 B2 * | 4/2022 | Bachus ................. A61F 2/2814 |
| 2002/0038148 A1 | 3/2002 | Fernandez et al. |
| 2003/0109878 A1 | 6/2003 | Grundei |
| 2005/0214714 A1 | 9/2005 | Wohrle |
| 2007/0030891 A1 | 2/2007 | Franz |
| 2007/0060891 A1 | 3/2007 | Skiera et al. |
| 2008/0200995 A1 | 8/2008 | Sidebotham |
| 2009/0187256 A1 | 7/2009 | Rauguth et al. |
| 2010/0222893 A1 | 9/2010 | Dorr et al. |
| 2011/0190907 A1 | 8/2011 | Porter et al. |
| 2011/0257758 A1 | 10/2011 | Smith et al. |

FOREIGN PATENT DOCUMENTS

| | | |
|---|---|---|
| DE | 102009027255 A1 | 8/2010 |
| EP | 1378215 A1 | 1/2004 |
| EP | 1529501 B1 | 7/2006 |
| JP | 9507143 | 7/1997 |
| JP | 2003535643 A | 12/2003 |
| WO | 2008026316 A1 | 3/2008 |
| WO | 2008092967 A1 | 8/2008 |
| WO | 2009105535 A1 | 8/2009 |
| WO | 2013048589 A1 | 4/2013 |
| WO | 2014015303 A1 | 1/2014 |

OTHER PUBLICATIONS

International Search Report, issued on related application No. PCT/US2012/041112; mailed Mar. 13, 2013.
Titanium Alloys in Medical Applications The Titanium Information Group (2003) pp. 1-3.

* cited by examiner

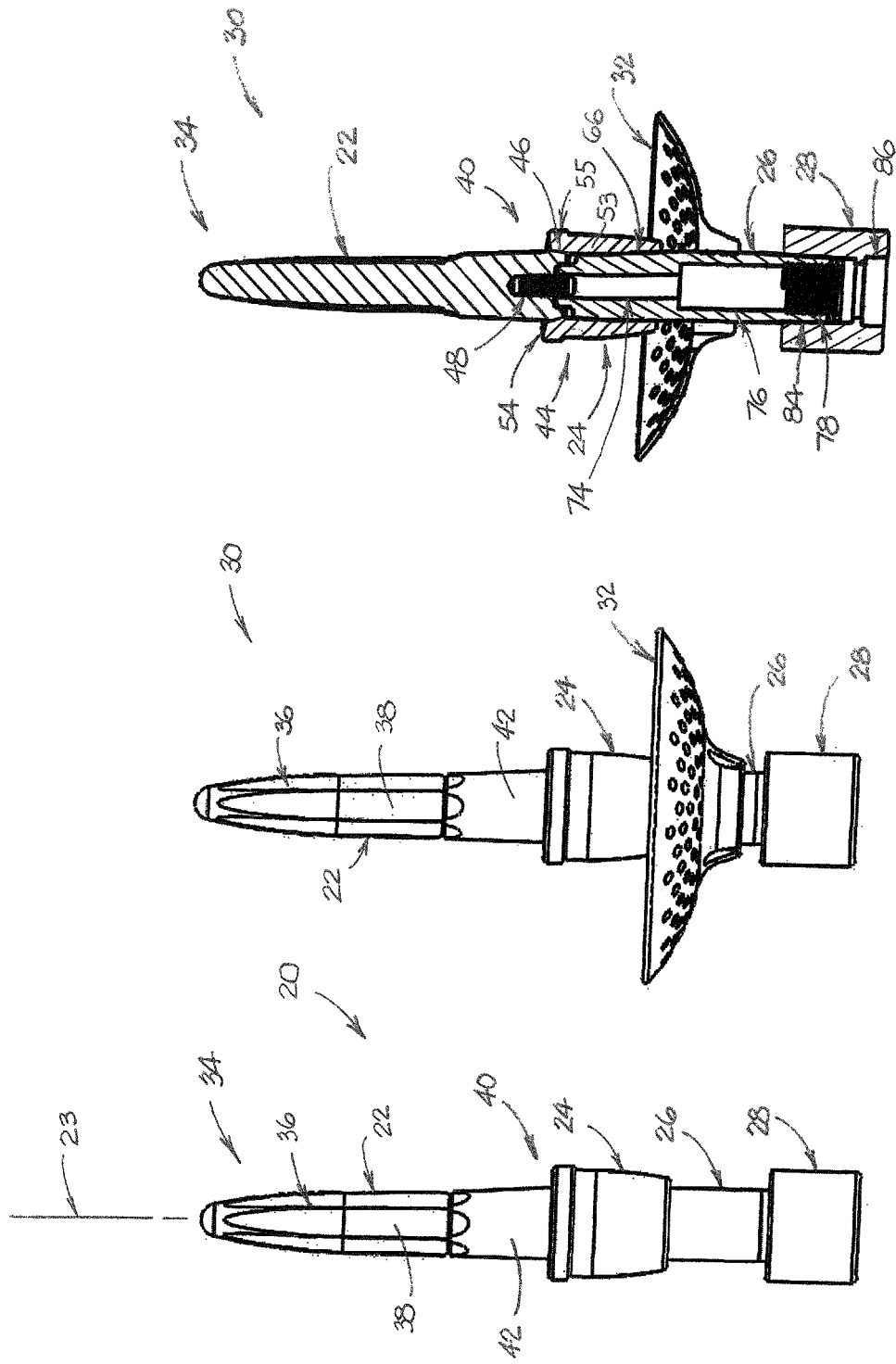

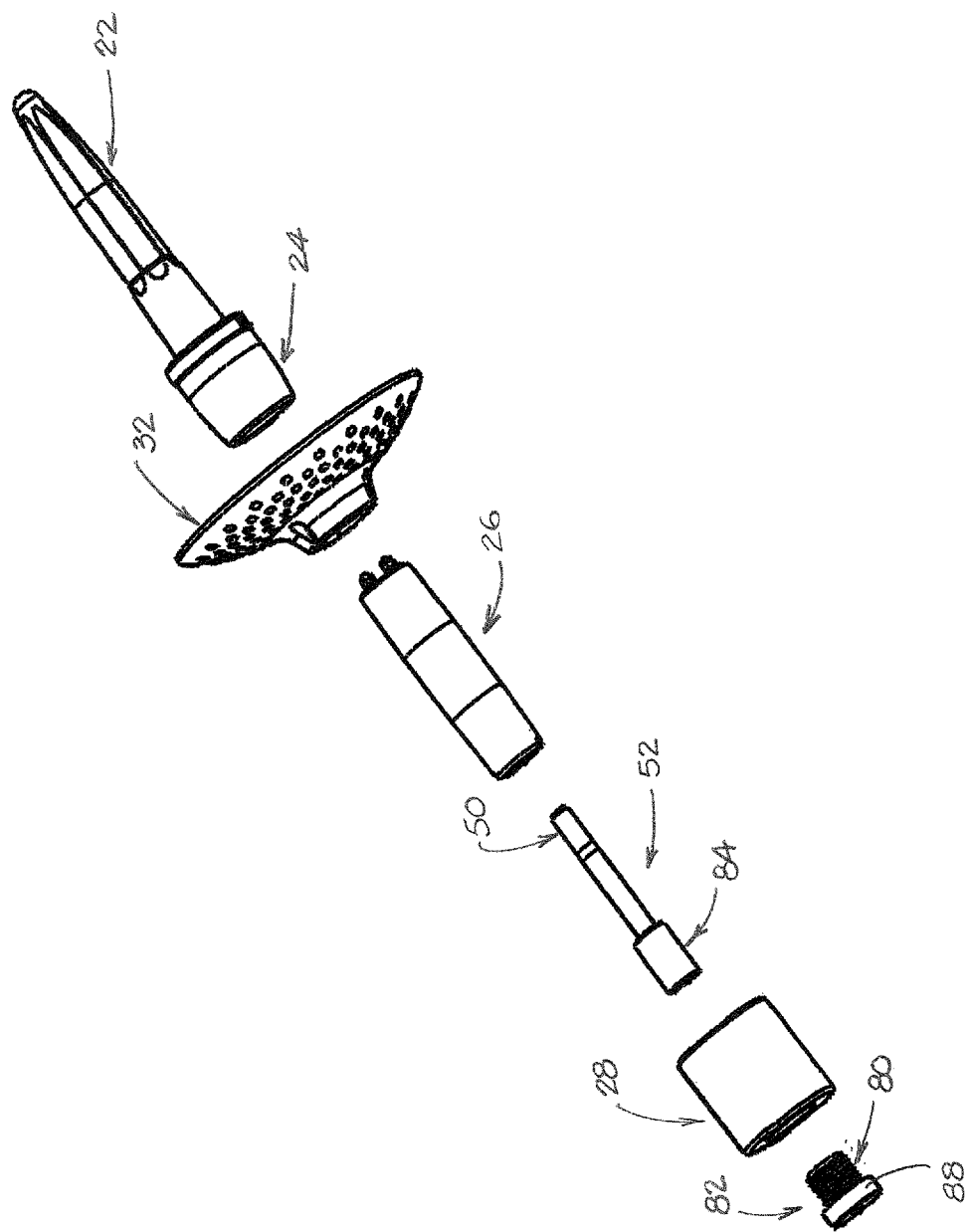

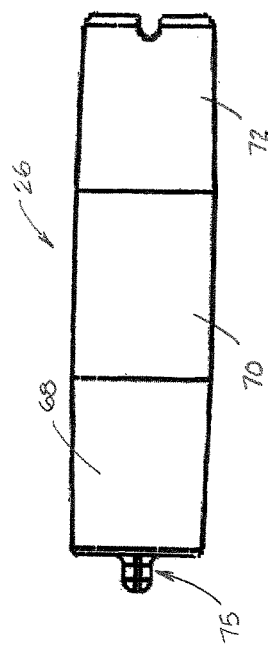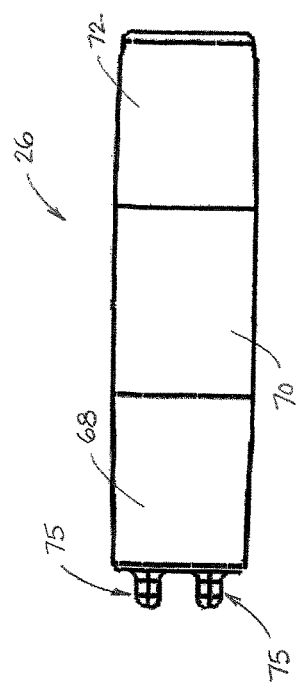

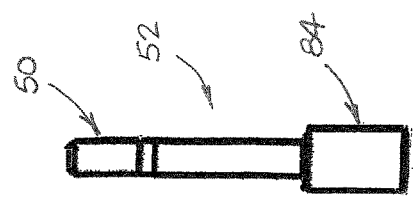
FIGURE 15
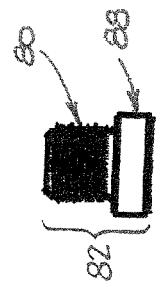
FIGURE 16
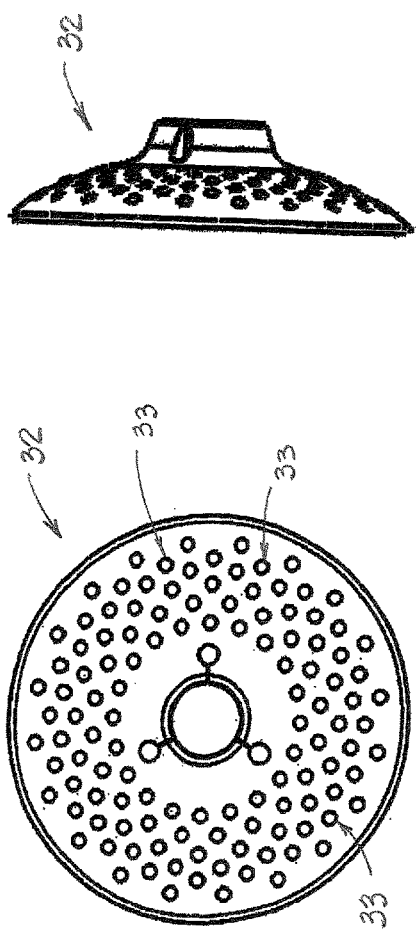
FIGURE 13
FIGURE 12
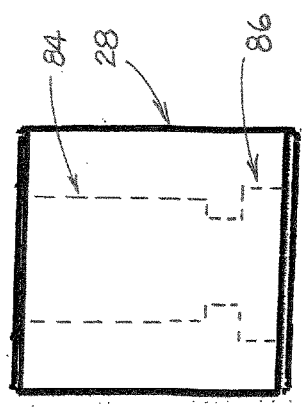
FIGURE 14

PERCUTANEOUS OSSEOINTEGRATED IMPLANT ASSEMBLY FOR USE IN SUPPORTING AN EXO-PROSTHESIS

CROSS-REFERENCE TO RELATED APPLICATIONS

This application is continuation of U.S. application Ser. No. 16/383,363, filed on Apr. 12, 2019, now U.S. Pat. No. 11,298,231, which is a divisional of U.S. application Ser. No. 15/256,731, filed on Sep. 5, 2016, which is a continuation of U.S. application Ser. No. 14/181,029, filed Feb. 14, 2014, now U.S. Pat. No. 9,433,305, which is a continuation-in-part of U.S. patent application Ser. No. 14/123,719 which was filed on Dec. 3, 2013 as the U.S. National Phase Application of PCT/US2012/041112, and issued as U.S. Pat. No. 9,668,889 which was filed on Jun. 6, 2012. The PCT Application claims priority from U.S. Provisional Patent Application No. 61/493,914, filed on Jun. 6, 2011, U.S. Provisional Patent Application No. 61/594,815, filed on Feb. 3, 2012, and U.S. Provisional Patent Application No. 61/622,783, filed on Apr. 11, 2012. Each of the aforementioned patent applications is hereby incorporated by reference herein in its entirety.

STATEMENT OF GOVERNMENT SUPPORT

This invention was made with United States government support under Grant Numbers HD061014 and AR058356 awarded by the National Institutes of Health and Grant Numbers W81XWH-06-1-0574 and W81XWH-05-1-0628 awarded by the Army/MRMC. The government has certain rights in this invention.

BACKGROUND OF THE INVENTION

Field of the Invention

This invention generally relates to implant assemblies that are adapted to be securely attached to a long bone and to support an exo-prosthesis. More particularly, the invention relates to such assemblies that area adapted for attachment to a long bone by osseointegration.

Description of the Related Technology

Amputation of limbs can occur as a result of trauma or surgical intervention. Currently, despite its limitations, socket technology remains the standard of care for attachment and/or docking of exo-prosthetic devices to a residual amputated limb of a patient. Recent clinical reviews of amputees with socket prosthetics have suggested that between 8% and 50% of amputees with socket prosthetics suffer from one or more dermatological pathologies that require temporary suspension of use of a prosthetic. The inability of these amputees to consistently use their prosthetics represents a significant decrease in their quality of life. In lower limb amputees, the limitations on usage of a prosthetic increase the susceptibility of the amputees to additional co-morbidities. Many pathologies related to current socket prosthetic designs possess interconnected biochemical and biomechanical cues.

High infection rates remain a major limitation of current prosthetic systems. A high infection rate is often associated with the lack of a skin seal at the skin-implant interface that provides an ideal direct path for opportunistic bacterial invasion to the stomal tissue and often results in sinus tract formation. This may subsequently result in deep infection and bone loss requiring implant removal. Because of the rapid evolution of antibiotic-resistant pathogens as well as the high incidence of methicillin-resistant *Staphylococcus aureus* (MRSA) cases, these infections may not be treatable with conventional antibiotic therapy. Commonly, the outcome is device removal and further loss of bone and soft tissue resulting in shortening of the residual limb.

Therefore, what is needed in the art is an inherently adaptable, modular percutaneous osseointegrated prosthetic implant assembly that permits formation of a seal at the implant-skin interface, reduces dermatological complications associated with socket prosthetics, improves proprioception, extends the periods during which an exo-prosthesis can be worn, and reduces energy expenditure of the amputee wearing the prosthetic, thereby improving the overall quality of life for the amputee.

SUMMARY

The invention comprises an implant assembly for a long bone, which assembly is adapted to support an exo-prosthesis. The assembly includes a stem having a proximal end and a distal end, a subdermal component that is adapted for attachment to the distal end of the stem, and a percutaneous post. The proximal end of the stem is adapted to be received in a surgically prepared medullary canal of the long bone, and the distal end has a surface that is adapted to promote bone ingrowth. The subdermal component includes a proximal portion and a fixation surface. The proximal portion of the subdermal component is adapted for attachment to the distal end of the stem. At least one of the distal end of the stem and the proximal portion of the subdermal component defines a collar that is adapted to engage an osteotomy created by a cut through the long bone that is generally perpendicular to the longitudinal axis of the long bone. The percutaneous post has a proximal end that is adapted to be attached to the subdermal component.

In order to facilitate an understanding of the invention, the preferred embodiments of the invention and the best mode known by the inventors for carrying out the invention are illustrated in the drawings, and a detailed description thereof, as well as a description of presently contemplated alternatives, follows. It is not intended, however, that the invention be limited to the particular embodiments described or to use as specifically described herein. Therefore, the scope of the invention contemplated by the inventors includes all equivalents of the subject matter described herein, as well as various modifications and alternative embodiments such as would ordinarily occur to one skilled in the art to which the invention relates. The inventors expect skilled artisans to employ such variations as seem to them appropriate, including the practice of the invention otherwise than as specifically described herein. In addition, any combination of the elements, components and steps of the invention described herein in any possible variation is encompassed by the invention, unless otherwise indicated herein or clearly excluded by context.

BRIEF DESCRIPTION OF THE DRAWINGS

The presently preferred embodiments of the invention are illustrated in the accompanying drawings, in which like reference numerals represent like parts throughout, and in which:

FIG. 1 is a side view of a first embodiment of the invention.

FIG. 2 is a side of the embodiment shown in FIG. 1, showing the addition of a stoma shield.

FIG. 3 is a sectional view of the embodiment shown in FIG. 2.

FIG. 4 is a partially exploded view of the embodiment of FIGS. 2 and 3.

FIG. 10 is a side view of the embodiment of the percutaneous post that is illustrated in FIGS. 1-4.

FIG. 11 is a side view of the percutaneous post of FIG. 10, which view is rotated 90° about the long axis of the post from that shown in FIG. 10.

FIG. 12 is a front view of the stoma shield that is illustrated in FIGS. 2 and 3.

FIG. 13 is a side view of the stoma shield of FIG. 12.

FIG. 14 is a side view of adapter that is illustrated in FIGS. 1-4.

FIG. 15 is a side view of the assembly bolt that is illustrated in FIG. 4.

FIG. 16 is a side view of the adapter bolt that is illustrated in FIG. 4.

Figure 5:
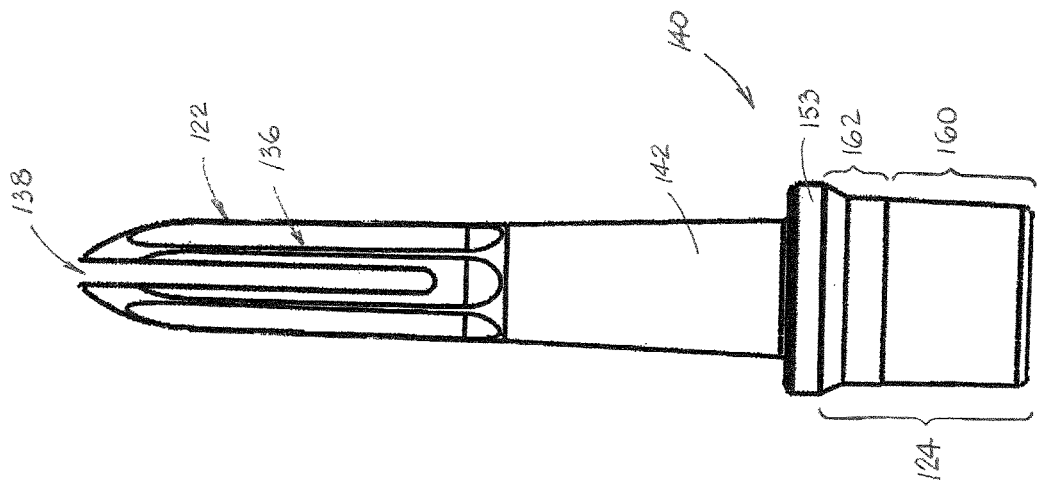
FIG. 5 is a side view of a second embodiment of the stem coupled to a second embodiment of the subdermal component.

The angles and dimensions depicted in the drawings may be exaggerated for clarity and, consequently, may not be to scale.

DETAILED DESCRIPTION OF CERTAIN INVENTIVE EMBODIMENTS

Among the advantages of the present invention is that it provides an implant assembly that can be readily installed in a long bone such as the femur. This assembly allows for the formation of a skin seal at the implant-skin interface. Thus, it is anticipated that this assembly will reduce dermatological complications associated with socket prosthetics and will improve proprioception. Furthermore, it is expected that this implant assembly will extend the period during which an exo-prosthesis can be worn, and will reduce the ambulation energy expenditure of the amputee wearing the prosthetic, thereby improving his/her overall quality of life. Other advantages and features of this invention will become apparent from an examination of the drawings and the ensuing description.

Notes on Construction

The use of the terms "a", "an", "the" and similar terms in the context of describing the invention are to be construed to cover both the singular and the plural, unless otherwise indicated herein or clearly contradicted by context. The word "or" as used herein means any one member of a particular list and also includes any combination of members of that list. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic. The terms "optional", "optionally" and similar terms mean that the subsequently described event or circumstance may or may not occur, and that the description includes instances where said event or circumstance occurs and instances where it does not.

The steps of all methods described herein can be performed in any suitable order unless otherwise specified herein or clearly indicated by context. The use of any and all examples or exemplary language (e.g., "such as") herein is intended merely to better illuminate the invention and not to place a limitation on the scope of the invention, unless otherwise indicated by the claims. Nothing in the specification should be construed as indicating any non-claimed element as essential to the practice of the invention. Ranges can be expressed herein as from "about" one particular value to "about" another particular value. Such an expression is intended to include a range from the one particular value to the other particular value, as well as ranges including variations in the particular values.

Several terms are specifically defined herein. These terms are to be given their broadest possible construction consistent with such definitions, as follows:

The term "subject" refers to an individual, and can include humans as well as other animals. The term "subject" does not denote a particular age or sex, and can include animals of either sex and of any age.

The term "insertional" refers to the end of a first component that is configured for insertion into a second component. For example, an "insertional" end of a component can be configured for insertion into a prepared site within a long bone or for insertion into an implant component.

The term "low energy surface" refers to a surface comprising or coated with one or more materials that are configured to inhibit adhesion and/or adsorption between the surface and other materials. For example, "low energy surfaces" as described herein permit little if any in-growth, integration, and/or adhesion between the surface and biological tissues, biological fluids, and bacteria. It is contemplated that the reduced bio-adhesion permitted by the "low energy surfaces" described herein can permit thorough post-operative drainage for improved wound healing and reduce the incidence of infection. Exemplary low energy surfaces include surfaces that comprise or are coated with hydrophobic materials (i.e., those having a 100°-150° contact angle) or superhydrophobic materials (i.e., those having >150° contact angle).

The term "soft tissue" refers to all or part of a subject's epidermis, dermis and underlying subcutaneous tissues.

Disclosed Embodiments

The following description of the invention is provided as an enabling teaching of the invention in its best, currently known embodiments. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Disclosed herein are implants, implant assemblies, and methods for securing an exo-prosthesis to a limb of a subject. It is contemplated that the disclosed implants, implant assemblies, and methods can be used to permit integration of bone and skin of the subject into an implant to which an exo-prosthesis is operably attached. It is further contemplated that the disclosed implants, implant assemblies, and methods can permit formation of a seal between the soft tissue of the subject and the implant, thereby minimizing the possibility of peri-prosthetic infections, both superficial soft tissue and muscle infections and deep bony infections. It is still further contemplated that the disclosed implants, implant assemblies, and methods can minimize post-implantation migration of the soft tissue of the subject, thereby reducing the likelihood of formation of a pocket between the skin of the subject and the implant. In particular applications, it is contemplated that the disclosed implants, implant assemblies, and methods can be used to allow military veterans and civilians who have experienced lower extremity amputation to a obtain a near pre-amputation activity level. Generally, it is contemplated that the above-mentioned objectives can be achieved through optimized selection of various characteristics of the implant assembly, such as, for example, surface characteristics of the various components described herein, to achieve a desired arrangement and/or orientation of the implant assembly to the bone and surrounding tissue of the subject, as well as a desired attachment between the implant and an exo-prosthesis.

As shown in FIG. 1, implant assembly 20 includes stem 22, subdermal component 24, percutaneous post 26 and adapter 28. Each of these components can be made of conventional surgical-quality metallic materials, including, for example and without limitation, titanium, cobalt chrome, and the like. FIGS. 2-4 illustrate implant assembly 30, which is essentially identical to implant assembly 20 except for the addition of stoma shield 32 (also illustrated in FIGS. 12 and 13). The stoma shield is preferably comprised of a flexible elastomeric material and includes a plurality of ventilation holes 33. It is adapted to fit over and provide a measure of protection for the amputation stump of a subject, as well as a means for protecting the exo-prosthetic from natural body fluid that may weep from the stoma during healing.

Figure 7:
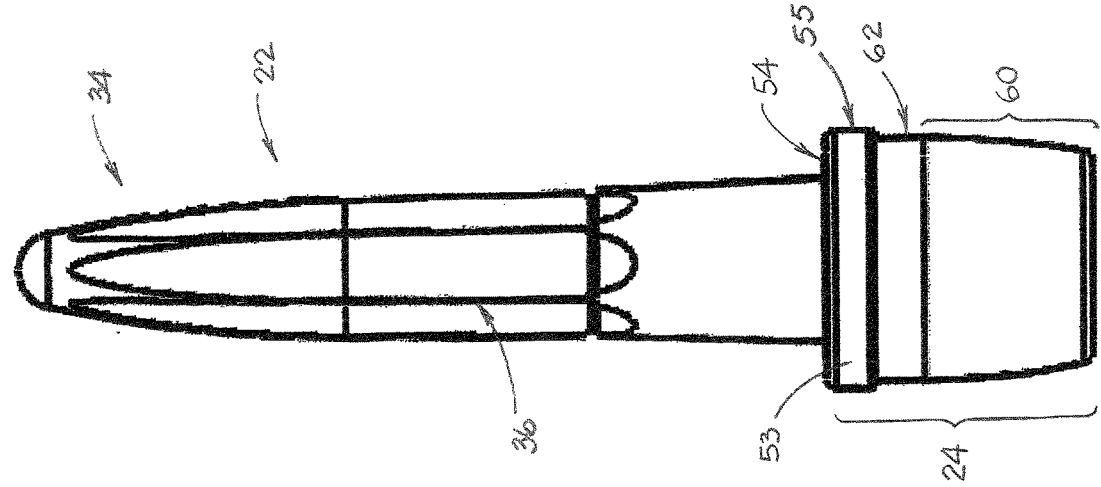
FIG. 7 is a side view of the stem and the subdermal component of the embodiment of FIGS. 1-4.

Stem 22, which is also illustrated in FIG. 7, has a proximal (or insertional) end 34 that is adapted to be received in a prepared hole that has been bored in the intramedullary cavity of a long bone such as the femur of a subject whose lower leg has been amputated. However, it is also contemplated that the disclosed methods, assemblies and components thereof can be used with any long bone within a tissue region of a subject, including, for example, a humerus of a subject. It is also contemplated that stem 22 can be securely received within the prepared hole such that the longitudinal axis 23 of the stem is substantially axially aligned with the longitudinal axis of the selected bone. In the embodiment of stem 22 that is illustrated in the drawings, splines 36 are provided to enhance fixation within the bone. Preferably, the stem includes a plurality of spaced splines 36 that are oriented substantially parallel to the longitudinal axis 23 of the stem. It is also contemplated that at least a portion of the outer surface 38 of the insertional or proximal end 34 of the stem 22 can be treated to obtain a desired surface roughness, thereby improving bone attachment.

Figure 6:
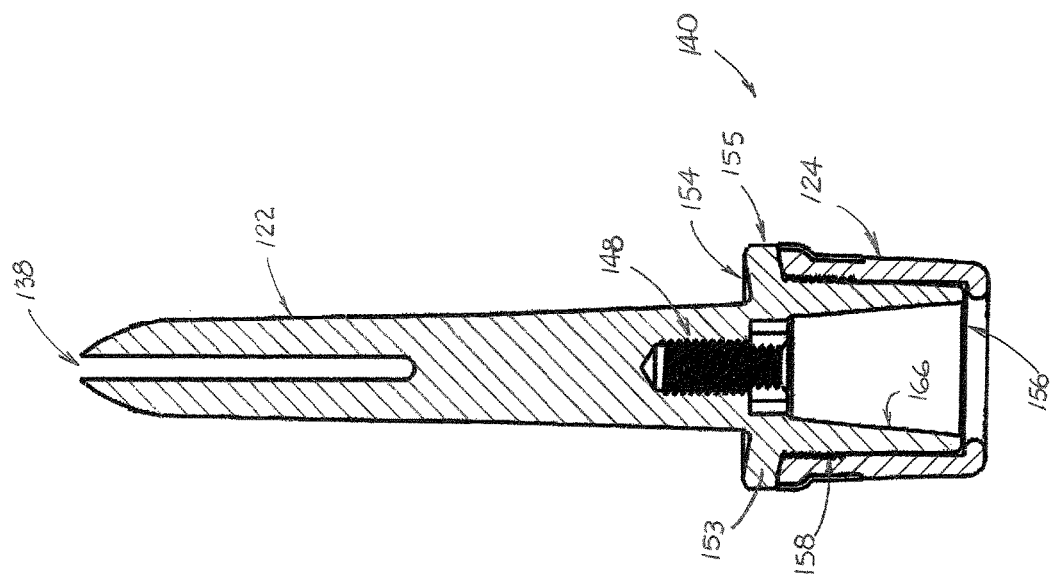
FIG. 6 is a sectional view of the embodiment shown in FIG. 5.
Figure 9:
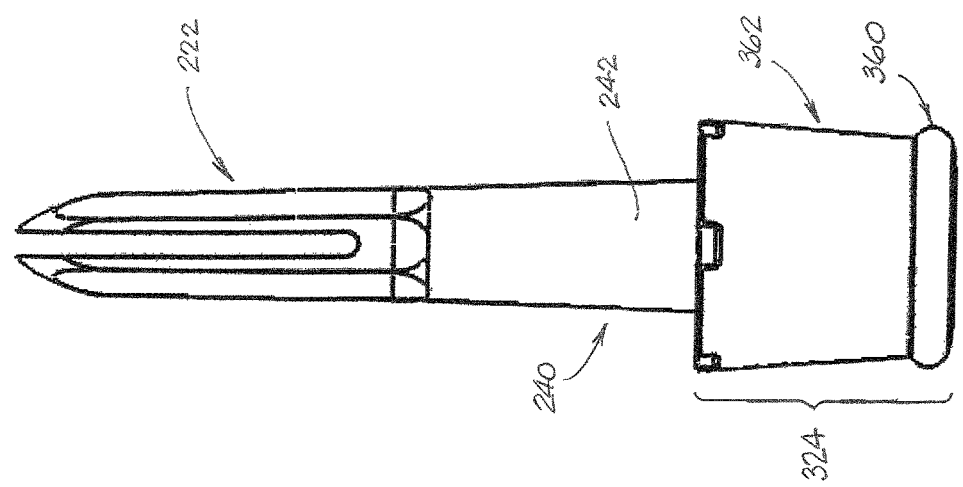
FIG. 9 is a side view of the stem of the embodiment of FIG. 8 coupled to a fourth embodiment of the subdermal component.
Figure 8:
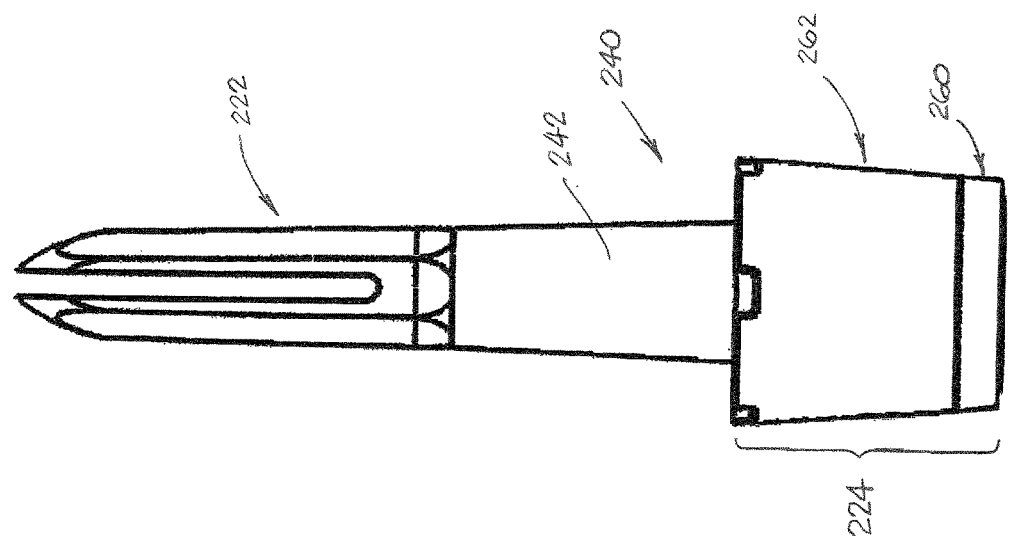
FIG. 8 is a side view of a third embodiment of the stem coupled to a third embodiment of the subdermal component.

A second embodiment of the stem is illustrated in FIGS. 5 and 6, and a third embodiment is illustrated in FIGS. 8 and 9. Stem 122 (shown in FIGS. 5 and 6) includes a plurality of longitudinal splines 136 and a slot 138 that is configured to promote fixation with the selected bone. Similarly, stem 222 (shown in FIGS. 8 and 9) includes a plurality of longitudinal splines 236 and a slot 238 that is configured to promote fixation with the selected bone. Optionally, stems 22, 122 and 222 can be configured to mimic physiological properties of the anatomical bow within a native bone, thereby reducing and/or limiting torsional displacement of the stem following implantation, and improving both short-term and long-term performance of the implant assembly.

Stem 22 is also provided with a distal end 40 having a surface 42 that is adapted to promote bone ingrowth. Stems 122 and 222 are each provided with similar distal ends 140 and 240 respectively and similar surfaces 142 and 242 respectively. Surface 42 preferably comprises a porous structure that is adapted to support osseointegration. This porous structure may be obtained by coating at least a portion of the distal end with a porous material using known methods for coating a substrate. Preferably, porous surface 42 comprises a continuous circumferential layer of porous material. Alternatively, porous surface 42 can comprise a plurality of porous sections that are spaced about an operative circumference of the distal end of the stem. Although not shown in the drawings, the porous surface 42 of the stem can be recessed relative to the outer surface of adjoining portions of the stem. It is contemplated that the porous surface 42 of the stem can be formed using known techniques. Preferably, porous surface 42 comprises porous titanium, and more preferably, substantially pure porous titanium. However, it is also contemplated that other medical grade porous metals, as well as porous polymers and ceramics, can be used as described herein. Preferably, the porous surface 42 of the stem can have a thickness ranging from about 0.5 mm to about 2.0 mm. It is also preferred that the porosity of the porous surface 42 of the stem can range from about 40% to about 80% and, more preferably, from about 50% to about 70%. It is also preferred that the size of each pore of the porous surface 42 can range from about 25 μm to about 1,000 μm and, more preferably, from about 40 μm to about 400 μm. However, as one will appreciate, it is contemplated that the desired porosity and pore size for the porous surface 42 can be selectively varied depending upon, for example and without limitation, the subject's bone condition, amputation causality, the age of the subject, the residual limb length, the time since initial injury, the time since amputation, the vascular health of the subject, and other factors.

It is contemplated that, upon secure receipt of stem 22 within the surgically prepared site, the porous surface 42 of distal end 40 of the stem can be configured to promote integration and ingrowth of the selected bone of the subject into the stem. It is further contemplated that such osseointegration (between the selected bone and the porous surface 42 of the stem 22) can lead to improvement in the post-surgery quality of life of the subject through improved proprioception (i.e., dynamic exo-prosthesis load sensation) and gait efficiency (i.e., improved physiologic energy expenditure). It is also contemplated that the modular design of the implant assembly described herein can provide a platform for further optimization of the design of the stem without the need for significant surgical intervention. For example, it is contemplated that the porous region can be limited in size so as to permit removal and/or revision of the stem with minimal loss or destruction of residual bone. It is further contemplated that, in the event of a bone infection following implantation of the stem, the stem can be removed, the surgically revised site can be allowed to drain, and a therapeutic treatment regimen can be executed without significant tissue loss or harm to the subject.

Assemblies 20 and 30 also include subdermal component 24 having a proximal end 44 that is adapted for attachment to the distal end of the stem. Preferably, the subdermal component is hollow. In the embodiment of the invention best illustrated in FIG. 3, terminal portion 46 of the distal end 40 of stem 22 is tapered and adapted to be received in a corresponding tapered portion of the proximal end 44 of the subdermal component. In this embodiment of the invention, it is also preferred that distal end 40 of the stem includes threaded bore 48 and that proximal portion 50 of assembly bolt 52 (shown in FIGS. 4 and 15) is provided with corresponding male threads so that the assembly bolt may be attached by threaded engagement to the stem. In the embodiments of the invention illustrated in the drawings, at least one of the distal end of the stem and the proximal portion of the subdermal component defines a collar that extends radially outwardly from adjacent structures and is adapted to engage an osteotomy created by a cut through the long bone that is generally perpendicular to the longitudinal axis of the long bone. Thus, in the embodiment of the invention illustrated in FIGS. 1-4 and 7, subdermal component 24 includes a proximal end portion that defines a collar 53 which extends radially outwardly from the adjacent distal end 40 of the stem and is adapted to engage an osteotomy created by a cut through the long bone that is generally perpendicular to the longitudinal axis of the long bone. In the embodiment of the invention illustrated in FIGS. 5 and 6, the distal end 140 of the stem includes a proximal collar 153 that extends radially outwardly from adjacent portions of the stem and is adapted to engage an osteotomy created by a cut through the long bone that is generally perpendicular to the longitudinal axis of the long bone.

The proximal collar portion of either the stem or the subdermal component can be configured to form a flush interface and/or seal with the selected bone. It is further contemplated that the flush interface and/or seal formed between the collar and the cut bone can permit transfer of ground reaction forces substantially directly to the skeletal system of the subject, thereby preventing bone atrophy. Preferably, the proximal collar portion includes a substantially flat surface 54 or 154 that extends substantially perpendicularly relative to the longitudinal axis of the stem. However, it is contemplated that the proximal collar portion 53 or 153 can include a chamfered surface or have another surface shape, provided the collar surface permits formation of a flush interface with the cut in the bone. It is further contemplated that the proximal collar portion can be shaped to substantially conform to the shape of adjacent tissues within the subject. In one embodiment, the proximal collar portion can have a substantially circular cross-sectional profile about the longitudinal axis of the stem. However, it is also contemplated that the proximal collar portion can have an elliptical or other cross-sectional profile that permits formation of a flush interface with the selected bone and provides desired support to the selected bone. Optionally, the radially outer surface 55 or 155 of the proximal collar portion can be outwardly tapered, sloped, and/or curved with respect to the longitudinal axis of the stem so as to substantially conform to the shape of adjacent tissue structures within the subject. In addition, at least a portion of the surface of the collar that is adapted to abut bone can comprise a porous material as described herein in order to facilitate and increase bone integration, thereby ensuring contiguous load transmission between the implant assembly and the distal end of the bone. It is further contemplated that appropriately scaled load transmission at this interface can prevent bone resorption due to stress shielding at the distal bone end of the transected bone and can promote bone hypertrophy more proximally.

Distal end 140 of stem 122 also includes downwardly depending portion 156 below proximal collar portion 153. At least a portion 158 of the outer surface of this downwardly depending portion is provided with male threads that are adapted to mate with corresponding female threads on subdermal component 124, so that the subdermal component can be attached the stem by threaded engagement as shown in FIG. 6. The distal end 140 of stem 122 also includes threaded bore 148 (similar to threaded bore 48 in stem 22), so that proximal end 50 of assembly bolt 52 (shown in FIGS. 4 and 15), which is provided with corresponding male threads, may be attached by threaded engagement to the stem. Also contemplated within the scope of the invention are other mechanisms by which the subdermal component can be attached to the stem that are known to those having ordinary skill in the art to which the invention relates.

As indicated by comparing FIGS. 5-9, the configuration of the subdermal component may vary. In some embodiments of the subdermal component, the portion below the collar is substantially cylindrical. In other embodiments, the configuration of the subdermal component may be tapered or concave towards its distal end, or convex towards its distal end. In some embodiments of the invention, the proximal end of the subdermal component includes an abutment surface that permits formation of a flush interface with the cut in the bone but does not extend radially outwardly from adjacent portions of the subdermal component. In other embodiments, the proximal end portion of the subdermal component may have a larger dimension than adjacent portions.

Preferably, the outer surfaces of the subdermal component are provided with one or more surface treatments to facilitate a secure attachment of the implant assembly to the long bone and to permit the formation of a seal between the soft tissue of the subject and the implant assembly, thereby minimizing the possibility of infection at or below the interface between the implant assembly and the soft tissue of the subject. In some embodiments of the invention, the entire outer surface of the subdermal component may comprise a fixation surface that is adapted to facilitate the formation of a seal between the soft tissue of the subject and the implant assembly. In other embodiments, the subdermal component may be provided with an outer surface having discrete areas or portions with differing surface treatments, including a fixation surface and a low energy surface. In some embodiments, the subdermal component may have a transition surface between the fixation surface and the low energy surface. Thus, as best shown in FIG. 7, distal portion 60 is provided with a low energy surface that is adapted to inhibit bio-adhesion, proximal collar portion 53 is provided with a fixation surface 55 that is adapted to promote soft tissue fixation, and intermediate portion 62 is provided with a transition surface between the fixation surface and the low energy surface. In similar fashion, distal portion 160 of subdermal component 124 (shown in FIG. 5) is provided with a low energy surface that is adapted to inhibit bio-adhesion, proximal collar portion 153 is provided with a fixation surface 155 that is adapted to promote soft tissue fixation, and intermediate portion 162 is provided with a transition surface between the fixation surface and the low energy surface. In some embodiments of the subdermal component, there is no portion having a transition surface. Thus, as shown in FIG. 8, distal portion 260 of subdermal component 224 is provided with a fixation surface that is adapted to promote soft tissue fixation and proximal portion 262 is provided with a low energy surface that is adapted to inhibit bio-adhesion. Similarly, as shown in FIG. 9, distal portion 360 of subdermal component 324 comprises a ring of larger diameter than the adjacent part of proximal portion 362, which ring is provided with a fixation surface that is adapted to promote soft tissue fixation. In this embodiment of the invention, proximal portion 362 is provided with a low energy surface that is adapted to inhibit bio-adhesion.

The low energy surface of the distal portion of the subdermal component (such as distal portion 60 of subdermal component 24) comprises a surface that has been treated to increase its hydrophobic characteristics. Such a surface may be obtained by treating the surface by a process selected from the group consisting of abrasive blasting, burnishing, grinding, buffing, chemical vapor deposition and combinations of such processes. The fixation surface of the proximal portion of the subdermal component (such as fixation surface 55 of proximal collar portion 53 of subdermal component 24) is adapted to facilitate soft tissue integration. Such a surface may be obtained by treating the surface to produce or apply a porous structure such as a structure that is adapted to support osseointegration. The transition surface of the intermediate portion of the subdermal component (such as intermediate portion 62 of subdermal component 24) comprises a surface that has been treated to increase its surface energy relative to the low energy surface, yet still have a lower surface energy than the fixation surface. Such a surface may be obtained by treating the surface by a process selected from the group consisting of abrasive blasting, burnishing, grinding, buffing, chemical vapor deposition and combinations of such processes.

The inner surface of the subdermal component is preferably tapered to receive the correspondingly tapered proximal end portion 68 of percutaneous post 26. Thus, inner surface 66 of subdermal component 24 is preferably tapered to receive the proximal end portion of the percutaneous post, and the inner surface 166 of downwardly depending portion 156 of stem 122 is also preferably tapered to receive the proximal end portion of the percutaneous post. The taper of these surfaces, and that of other tapered surfaces described herein, can comprise conventional Morse tapers. Alternatively, such surfaces may be tapered relative to the longitudinal axis 23 of the stem 22 at an angle ranging from about 1.5° to about 4° and, more preferably, from about 2.5° to about 3.5°.

Percutaneous post 26 also includes a central portion 70 that is preferably of generally cylindrical configuration and a tapered distal portion 72. In the embodiments of the invention illustrated in the drawings, percutaneous post 26 is provided with a central bore, as shown in FIG. 3. This central bore has a proximal portion 74 of a first diameter and a distal portion 76 of a second diameter. Preferably, the proximal end 68 of percutaneous post 26 is also provided with one or more anti-rotation tabs 75, shown in FIGS. 10 and 11 (two are shown in the drawings) that allow for transmission of assembly torques through the tabs and the percutaneous post and away from the bone-implant interface.

Preferably, the percutaneous post is provided with a low energy surface such as is provided on the distal portion of the subdermal component. Such surface may be obtained by treating it to reduce the likelihood of biological attachment, such as by treating the surface by a process selected from the group consisting of abrasive blasting, burnishing, grinding, buffing, chemical vapor deposition and combinations of such processes. The distal end 78 of distal portion 76 of the percutaneous post is threaded to receive threaded end 80 of adapter bolt 82.

The implant assembly also preferably includes an adapter 28 having a central bore which includes a first portion 84 and a second portion 86, as shown in FIG. 3. The first portion 84 of the central bore is preferably tapered so as to receive distal portion 76 of the percutaneous post, whereas the second portion 86 of the central bore is shaped so as to receive head 88 of adapter bolt 82. A plurality of adapters may be included to provide functional interfaces with various exo-prostheses, or a single adapter may be provided for a plurality of exo-prostheses.

The implant assembly also preferably includes an assembly bolt 52 comprising a proximal portion 50 with a threaded proximal end that is adapted to engage threaded bore 48 in the distal end of the stem. Proximal portion 50 has a proximal diameter that is adapted to be received in bore 74 in the proximal portion of the central bore of percutaneous post 26 so that the threaded end of assembly bolt 52 may engage threaded bore 48 in the distal end of the stem. Assembly bolt 52 also has a distal portion 84 having a distal end and a distal diameter that is adapted to be received in distal portion 76 of the central bore of the percutaneous post, said distal end being provided with a hex-head, locking nut or other tool-engagement feature so that a tool such as a wrench, nut driver or screwdriver may be employed to tighten the assembly bolt into threaded bore 48 in the distal end of the stem. The head 88 of adapter bolt 82 may also be provided with a hex-head, locking nut or other tool-engagement feature so that a tool such as a wrench, nut driver or screwdriver may be employed to tighten the adapter bolt into the threaded bore in the distal end 78 of the percutaneous post.

The implant assembly described herein can be used in a method of securing an exo-prosthesis to a selected bone of a limb of a subject. It is contemplated that a medullary cavity of the selected bone is surgically prepared for receipt of the implant assembly. The stem, subdermal component and percutaneous post can be assembled together by means of the assembly bolt so that the stem may be positioned within the prepared site of the selected bone so that a collar defined by at least one of the distal end of the stem and the proximal portion of the subdermal component engages an osteotomy created by a cut through the long bone that is generally perpendicular to the longitudinal axis of the long bone.

Upon secure receipt of the stem within the prepared site such that the longitudinal axis of the stem is substantially axially aligned with the longitudinal axis of the selected bone, the stem can be configured to promote integration of the selected bone of the subject and the subdermal component can be configured to promote soft tissue fixation of the subject into the assembly. More particularly, it is contemplated that the structures of these components can promote integration of bone and soft tissue of the subject into the assembly such that a seal is formed between the soft tissue of the subject and the implant assembly. It is further contemplated that the seal that is formed between the soft tissue of the subject and the implant assembly can reduce the likelihood of infection in the subject and minimize the possibility of an open path of access from the exterior to the osteotomy. The optional stoma shield and adapter can then be attached to the implant assembly to allow for secure connection to an exo-prosthesis by means such as are known to those having ordinary skill in the art to which the invention relates.

It is contemplated that one or more of the individual components of the implant assembly described herein can be provided in the form of a kit. It is further contemplated that the respective components of the implant assembly described herein can be labeled or color-coded to indicate the particular sizing and/or attachment features of the component that enable a surgeon or other medical practitioner to determine whether the component is appropriate use in a particular procedure and/or whether the component is complementary in size and/or function to other components of an implant assembly.

Although this description contains many specifics, these should not be construed as limiting the scope of the invention but as merely providing illustrations of the presently preferred embodiments thereof, as well as the best mode contemplated by the inventors of carrying out the invention. The invention, as described herein, is susceptible to various modifications and adaptations, as would be understood by those having ordinary skill in the art to which the invention relates, and the same are intended to be comprehended within the meaning and range of equivalents of the appended claims.

What is claimed is:

1. A method of securing an exo-prosthesis to a selected bone of a limb of an individual in need thereof, comprising:
    preparing a medullary cavity of a selected long bone for receipt of at least a portion of an implant assembly;
    inserting at least a proximal end of a stem of the implant assembly within the prepared medullary cavity of the selected bone, a distal end of the stem comprising a substantially flat collar having a substantially flat surface that extends perpendicular to a longitudinal axis of the selected long bone and that engages the selected long bone perpendicular to the longitudinal axis of the selected long bone, thereby forming a direct seal with the selected long bone;
    attaching a proximal portion of a subdermal component to the distal end of the stem, the subdermal component comprising:
        a low energy surface configured to inhibit bio-adhesion disposed on the proximal portion of the subdermal component; and
        a distal portion comprising a fixation surface having a porous structure configured to promote soft tissue fixation; and
    attaching a proximal end of a percutaneous post to the subdermal component.

2. The method of claim 1, further comprising attaching a flexible elastomeric stoma shield comprising a plurality of ventilation holes to the percutaneous post of the implant assembly such that the stoma shield is disposed over an amputation stump of the limb of the individual.

3. The method of claim 1, wherein the distal end of the stem comprises a circumferential porous titanium coating.

4. The method of claim 3, wherein the circumferential porous titanium coating is recessed relative to outer surfaces of adjoining portions of the stem.

5. The method of claim 1, wherein the stem of the implant assembly further comprises a plurality of splines, each extending substantially parallel to a longitudinal axis of the stem.

6. The method of claim 1, wherein the stem of the implant assembly further comprises a central slot that substantially bisects the proximal end of the stem of the implant assembly and thereby promotes fixation within the selected long bone.

7. The method of claim 1, further comprising:
    attaching a proximal end of an adapter to a distal end of the percutaneous post; and
    attaching a distal end of the adapter to the exo-prosthesis.

8. The method of claim 1, wherein:
    the proximal portion of the subdermal component comprises a radial dimension that is greater than a radial dimension of the distal end of the stem; and
    a distal portion of the subdermal component has a radial dimension that is greater than a radial dimension of the proximal portion of the subdermal component.

9. The method of claim 1, wherein at least a portion of the subdermal component has a concave profile.

10. The method of claim 1, wherein at least a portion of the subdermal component has a convex profile.

11. The method of claim 1, wherein the subdermal component is substantially cylindrical.

12. The method of claim 1, wherein a surface of the distal end of the stem comprises a porous structure configured to support osseointegration.

13. The method of claim 6, wherein the low energy surface of the proximal portion of the subdermal component has been treated to increase its hydrophobic characteristics.

14. The method of claim 1, wherein the low energy surface of the proximal portion of the subdermal component is formed utilizing a process selected from the group consisting of abrasive blasting, burnishing, grinding, buffing, chemical vapor deposition and combinations of such processes.

15. The method of claim 1, wherein the porous structure of the fixation surface is further configured to support osseointegration.

16. The method of claim 1, wherein the subdermal component comprises an intermediate portion disposed between the distal portion and the proximal portion and comprising a transition surface having a variable porosity configured to increasingly promote bio-adhesion and/or soft tissue fixation along a length of extension from the low energy surface to the fixation surface.

17. The method of claim 16, wherein the transition surface of the intermediate portion of the subdermal component has been treated to increase its hydrophobic characteristics relative to the fixation surface.

18. The method of claim 16, wherein the transition surface of the intermediate portion of the subdermal component is formed utilizing a process selected from the group consisting of abrasive blasting, burnishing, grinding, buffing, chemical vapor deposition and combinations of such processes.

19. The method of claim 1, wherein:
    the proximal end of the percutaneous post comprises at least one anti-rotation tab extending proximally away from the proximal end; and
    the attaching the proximal end of the percutaneous post to the subdermal component comprises coupling the at least one anti-rotation tab to the subdermal component.

20. The method of claim 1, wherein preparing the medullary cavity comprises performing an osteotomy by creating a cut through the selected long bone that is generally perpendicular to a longitudinal axis of the selected long bone.

* * * * *